United States Patent [19]

Viebach et al.

[11] Patent Number: 5,181,512
[45] Date of Patent: Jan. 26, 1993

[54] LITHOTRIPTER INCLUDING A HOLDING DEVICE FOR AN ULTRASOUND LOCATING TRANSDUCER

[75] Inventors: Thomas Viebach, Paehl; Rainer Kreibich; Bernd Nuber, both of Munich; Robert Pauker, Frontenhausen; Alexander Hesse, Munich, all of Fed. Rep. of Germany

[73] Assignee: Dornier Medizintechnik GmbH, Fed. Rep. of Germany

[21] Appl. No.: 629,121

[22] Filed: Dec. 17, 1990

[30] Foreign Application Priority Data

Dec. 18, 1989 [DE] Fed. Rep. of Germany ....... 3941683

[51] Int. Cl.⁵ .............................................. A61B 17/22
[52] U.S. Cl. ............................ 128/660.03; 128/24 EL
[58] Field of Search ....................... 128/24 EL, 660.03

[56] References Cited

U.S. PATENT DOCUMENTS 4,669,483 2/1987 Hepp et al. .................... 128/24 EL Primary Examiner—Ruth S. Smith

[57] ABSTRACT

A lithotripter in general includes a patient's rest, a therapeutic head for the production of shockwaves, an ultrasonic transducer, and a locating arm for moveably mounting the transducer on the therapeutic head; and an additional holding arm has one end connected to the patient's rest and the other end is releasably connectible to the transducer for providing for a dual holding of the transducer once a concrement has been located. The holder includes a structure for motion retardation, i.e. braking action on of the one end relative to the other end.

2 Claims, 1 Drawing Sheet

U.S. Patent        Jan. 26, 1993        5,181,512 ial patent application 39 15 382.7 (equivalent to U.S. Pat. No. 5,092,721). The lithotripter in this publication is associated with a locating arm at the therapeutic head. The term "locating arm" is used here for describing a holder for transducers or the like which are provided for finding a concrement using, e.g. ultrasonic equipment. The therapeutic head is the source for carrying out lithotripsy, i.e. for producing focussed shockwaves.

LITHOTRIPTER INCLUDING A HOLDING DEVICE FOR AN ULTRASOUND LOCATING TRANSDUCER

BACKGROUND OF THE INVENTION

The present invention relates to the treatment of patients by means of extracorporally produced shockwaves, particularly under utilization of contact-free lithotripsy; and more particularly the invention relates to lithotripters which include in each instance a focussing shockwave source, a patient's rest, and equipment for locating concrements in the body of human beings.

Equipment of the type to which the invention pertains generally is, for example, disclosed in German patent application 39 15 382.7 (equivalent to U.S. Pat. No. 5,092,721). The lithotripter in this publication is associated with a locating arm at the therapeutic head. The term "locating arm" is used here for describing a holder for transducers or the like which are provided for finding a concrement using, e.g. ultrasonic equipment. The therapeutic head is the source for carrying out lithotripsy, i.e. for producing focussed shockwaves.

The reference above disclose a geometric and physical relation in between a locating arm and a transducer mounted on the locating arm, and a so-called therapeutic focus as established by the shock-wave source. That relation between is variable and adjustable and can be tracked by means of appropriate measuring equipment.

The requirements as far as the mechanics of this device are concerned are considerably smaller than in the case of a locating arm that has no fixed connection in relation to the therapeutic head. However, it was found that this advantage is considerably diminished owing to the problems that result from the relative motion of the arm once it is fixed in relation to the patient. In addition, there is a problem that a kidney stone, e.g. which is imaged by way of an ultrasonic image, may be "lost" and still furthermore there is a problem of danger to the patient through collision between the body of the patient and the equipment.

Another possibility is given in German petty patent utility model 8800985 wherein it is disclosed that there is a locating arm affixed to the patient rest. This particular arrangement has the advantage that once the kidney stone has been located the arm can be fixed in some fashion to the surface of the patient without changing the position of the arm relative to the patient once the patient rest has been moved relative to the therapeutic head. The therapeutic head in turn remains coupled and the image portion as displayed in not varied; hence there is no danger of collision.

However, this arrangement has the disadvantage that the position of the therapeutic focus relative to the rest has to be determined and redetermined and adjusted, which is deemed a disadvantage. Aside from the inaccuracies in the acquisition of these parameters there is another possibility for error, namely any possible deformation of the patient rest under the load of the patient's weight which from that point of view remains unforeseeable but may introduce a locating error as regards the relation between the locating arm and the therapeutic head.

Affixing the locating arm for the ultrasonic locating transducer to the patient's rest is definitely disadvantageous as compared with connecting that locating arm to the therapeutic unit. The accuracy that is needed will suffer; on the other hand an arm affixed or connected to the therapeutic unit is more difficult to control during positioning. Moreover, developments in the past have led to a highly accurate transducer positioning arm that is realizable only by means of a very complex and usually rather heavy and unwielding mechanism. U.S. Pat. No. 4,669,438, corresponding to German patent 3427001 C1, discloses a lithotripter with a locating device that is affixed to a patient's rest; a second locating device is connected to the therapeutic head (FIG. 2 of that reference) but this duplication is relatively unwieldy in its own right. Moreover the range of permissible and possible motion of the second locating device is quite limited; there are just too many pieces of equipment in too limited a space.

For further information on the kinematics see U.S. patent applications, Ser. Nos. 513,612 and 513,613 now U.S. Pat. No. 5,078,124.

DESCRIPTION OF THE INVENTION

It is an object of the present invention to provide new and improved equipment for the treatment of a patient with extracorporally produced shockwaves wherein the locating of the body part to be treated and to be determined in relation to a focal point of the equipment can be determined in relation to the therapeutic unit but the control of the position of the shockwave producing head is fixed vis-a-vis the patient.

It is a specific object of the present invention to improve lithotripters which include a patient rest, a therapeutic head for the production of shockwaves and an ultrasonic transducer on a locating arm.

In accordance with preferred features of the present invention the objects are attained by maintaining as features for the contact-free lithotripsy, a patient's rest, a therapeutic head for the production of shockwaves and structure for positioning that head in relation to the patient on the rest; also maintained as a critical feature is an ultrasonic transducer being connected to a locating arm which is mounted on and movable in relation to the therapeutic head, and there are position sensing transducers for appropriately determining the position of the locating transducer relative to the therapeutic head.

In accordance with the preferred embodiment of the present invention, a holding device for the locating transducer is mounted on the patient's rest for holding the transducer. In other words the ultrasonic locating transducer is normally just adjustably mounted on the therapeutic head but once the locating procedure has been completed an additional holding is provided relative to the patient's rest by connecting the transducer to an articulating arm that is mounted on the patients rest and now there is a physical position relation established between the therapeutic head and the rest; a brake and motion retarding structure is interposed and included in the holding arm so that the transducer can at will be moved vis-a-vis the patient and his/her rest, but the brake retards any unintended motion and, for most instances, just holds the transducer immobile in relation to the patient on the rest.

It is therefore central to the invention to reconcile the two requirements made above concerning the relationship between locating equipment and the therapeutic head. It is the underlying principle of the invention to actually physically separate these two requirements. Owing to the braking or brakable holding equipment the ultrasonic head can now also be fixed vis-a-vis the patient's rest. As stated, a braking or brakable holding device is understood to be an arm which is equipped with a structure for braking the motion of individual parts of the arm in relation to each other.

It can thus be seen that the invention fulfills two contradictory tasks. First of all and as far as the locating procedure is concerned, the locating device acquires precise data on the position of the particular body part to be treated such as a concrement in relation to the focus of the treatment unit, i.e. the therapeutic device that is the lithotripter proper. The position and path acquisition system must accurately determine the position of the ultrasonic transducer on the locating arm relative to the therapeutic unit. Upon using a hinged arm one will preferably obtain this goal by fastening that locating arm directly to the therapeutic unit. These structure features are known per se and the above-noted problems encountered with this approach have been discussed.

The entire equipment is to be positioned or connected in some fashion to the patient or rest. Without further steps, one needs an additional position and path transducing and acquisition system in order to determine the relative position between the patient's rest, the therapeutic unit, and the locating equipment. Under such a conditions, however, there is an accumulation of errors from position acquisition of the locating device relative to the therapeutic unit and another position determination of the therapeutic unit in relation to the patient's rest. Possible mechanical uncertainties and inaccuracies are accumulative, and result in measuring errors or at least in a significant deterioration of the locating accuracy vis-a-vis the patient. Moreover, the locating device with its ultrasonic transducer should be movable in all directions and should not limit the mobility of the ultrasonic transducer by the doctor. Under these circumstances it is very clear that a small and lightweight, easily movable hinge arm is of advantage. As regards treatment control, the ultrasonic transducer must be positioned vis-a-vis the patient's body. That means that the organ to be treated must be imaged during treatment. The imaging is of course by an ultrasonic imaging device. In accordance with the invention the arm that carries the ultrasonic transducer is positively held by the brake in order to prevent positioning motions and deflections relative to the patient.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

The single FIGURE shows an example of the preferred embodiment for practicing the invention under best mode configurations.

Figure 1:
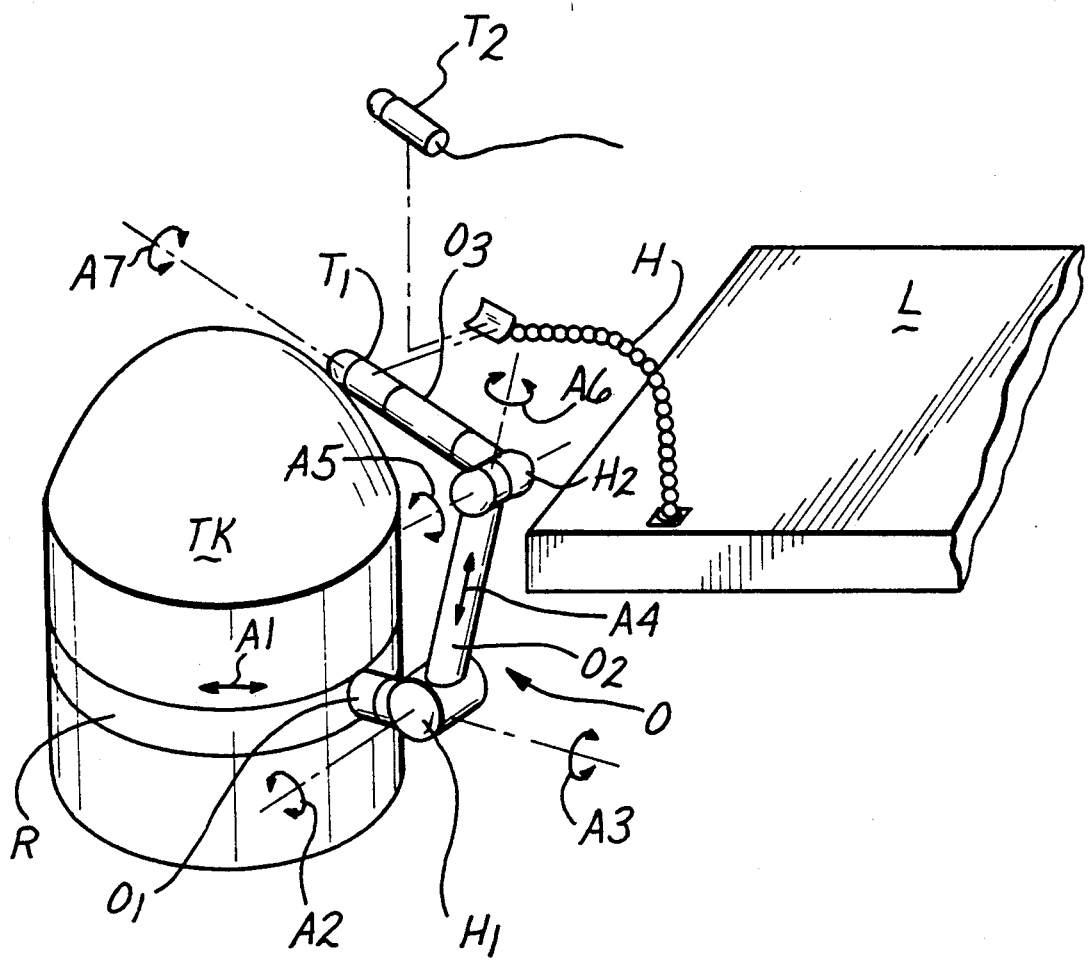

Proceeding now to the detailed description of the drawings, the FIGURE shows a therapeutic head TK which is mounted in a manner shown for example in the two U.S. patent applications referred to above. A locating arm O is connected to the therapeutic head and carries a ultrasonic imaging transducer T1. The connection is made as follows. A rotatable ring R is part of the therapeutic head TK and carries in radially outwardly extending direction an arm O1. These two parts together are a first component of the articulating arm assembly O. A hinge H1 connects arm O1 to a second arm O2, which in turn carries a hinge H2 for hingedly connecting a third arm O3 to arm O2. Arm O3 carries the transducer T1 for the ultrasonic locating structure.

The mobility of the locating arm O vis-a-vis the therapeutic head TK is indicated by various double arrows wherein arrow A1 indicates the motion of ring R around the central axis of the therapeutic head TK. A2 is a pivot motion around and by a hinge H1 that connects the middle arm O2 of the connection to the arm O1 that is connected to the ring R of the therapeutic head TK. Arrow A3 indicates a pivot motion of the latter hinge around the axis of arm O1 which is perpendicular to the axis of the pivot motion A2. The double arrow A4 indicates length extension and shortening of the middle arm O2 of the locating arm assembly O.

A curved double arrow A5 denotes the pivot motion of hinge H2 for the third arm O3 of the arm assembly O; as stated, arm O3 carries the transducer T1. The curved double arrow A6 denotes pivot motions of arm O3 around the axis of the middle arm O2; it can also be said that this turning motion A6 is carried out around the direction of motion indicated by the double arrow A4. The curved double arrow A7 indicates a motion of the transducer head T1 around its own axis which is the length axis of arm O3. The transducer T1 therefore is provided with many degrees of freedom of motion as regards treatment and positioning of the transducer relative to the patient.

Reference character L denotes the patient's rest, i.e. a bedlike structure on which the patient is positioned. Reference character H is now indicative of the inventive holding structure to which either the transducer T1 or another one, namely, T2 is or can be connected. In accordance with the invention the locating arm O is connected to the therapeutic head Tk through whose locating arm assembly O the position of both the ultrasonic transducer T1 and concrement made visible through the ultrasonic transducer T1 in relation to a particular imaging and coordinate system, can readily be measure in terms of coordinate values. This arm assembly with its integrated part and angle transducing equipment is exclusively provided for purposes of determining and acquiring the coordinate values. It is important that this piece of equipment is not subject to any braking.

The arm assembly O which is of very light weight; the position sensing transducers inside of arm and the parts and components of the arm assembly itself, are all very light; the transducer T1 is thus very easily movable in any and all directions. The task of positioning the transducer head T1 when necessary in a positive and position arresting fashion is carried out by a holding device or holder H that is affixed at one end to the patient's rest L. This particular holder H is an articulated arm of multiple link construction, each link member being, if desired, is movable (articulated) in relation to its adjoining and connecting link members but that movement is impeded or retarded or braked.

The free end of holder H is connectable to the locating arm assembly O particularly the transducer T1 thereof, whenever that is desired and needed. Alternatively another transducer T2, which is completely free from any other restraint, can be connected to that arm H. This is an optional feature. The essential part of the invention is to have a braking and brakable connection provided between the transducer on the locating arm normally only connected to the therapeutic head; after the locating procedure has been completed and the transducer T1 positioned on the patient; and after the coordinate values of the concrement (image) vis-a-vis the therapeutic focus has been determined, the position of transducer T1 is now position-arrested by the holder H and its motion impeding action. The braking equipment and the holding equipment for the brake is thus affixed to the patient's rest when problems of locating accuracies no longer enter into the picture!

The invention is not limited to the embodiments described above but all changes and modifications thereof, not constituting departures from the spirit and scope of the invention, are intended to be included.

We claim:

1. In a lithotripter which includes a patient's rest, a therapeutic head means for producing shockwaves, an ultrasonic transducer, and a locating arm for movably mounting the ultrasonic transducer, and means for determining the position of the ultrasonic transducer as mounted on the locating arm in relation to the therapeutic head means including pivot motions and rotating motions around a center axis of the therapeutic head means; the improvement comprising:

the locating arm being mounted to the therapeutic head means and being of articulated construction;

a connecting and holding arm being affixed with one end to said patient's rest and being releasably connected with its other end to said transducer so that prior to a connection of the transducer to the holding arm the transducer is independent from the patient's rest, while upon connecting the ultrasonic transducer to the holding arm the transducer has also a position that is then fixed with reference to the patient's rest, and the connecting and holding arm including means for retarding and braking any motion of the one end of the holding arm relative to the other end of the holding arm to thereby retard and brake any motion of the ultrasonic transducer when connected to the other end of the holding arm relative to the patient's rest.

2. The improvement as in claim 1 wherein said holding arm is a multiple link arm that is movable in all different directions.

* * * * *